United States Patent [19]

Kroll

[11] Patent Number: 5,620,469
[45] Date of Patent: Apr. 15, 1997

[54] STEPPED CARDIOVERSION SYSTEM FOR AN IMPLANTABLE CARDIOVERTER DEFIBRILLATOR

[75] Inventor: Mark W. Kroll, Minnetonka, Minn.

[73] Assignee: Angeion Corporation, Plymouth, Minn.

[21] Appl. No.: 321,389

[22] Filed: Oct. 11, 1994

[51] Int. Cl.⁶ .................................................. A61N 1/39
[52] U.S. Cl. .................................................. 607/7; 607/5
[58] Field of Search .................................. 607/4, 5, 7, 8, 607/14, 15

[56] References Cited

U.S. PATENT DOCUMENTS

| | | | |
|---|---|---|---|
| 3,747,605 | 7/1973 | Cook | 607/8 |
| 4,384,585 | 5/1983 | Zipes . | |
| 4,559,946 | 12/1985 | Mower | 607/5 |
| 4,693,253 | 9/1987 | Adams | 607/5 |
| 4,727,877 | 3/1988 | Kallok | 607/5 |
| 4,823,796 | 4/1989 | Benson | 607/8 |
| 4,830,006 | 5/1989 | Haluska et al. . | |
| 4,869,252 | 9/1989 | Gilli | 607/7 |
| 4,964,406 | 10/1990 | Carroll et al. | 607/5 |
| 5,014,697 | 5/1991 | Pless et al. | 607/7 |
| 5,161,527 | 11/1992 | Nappholz et al. | 607/14 |
| 5,163,428 | 11/1992 | Pless | 607/5 |
| 5,179,945 | 1/1993 | Van Hofwegan et al. | 607/5 |
| 5,188,105 | 2/1993 | Keimel | 607/5 |
| 5,201,865 | 4/1993 | Kuehn | 607/8 |
| 5,230,336 | 7/1993 | Fain et al. | 607/7 |
| 5,314,448 | 5/1994 | Kroll et al. | 607/5 |
| 5,318,591 | 6/1994 | Causey, III et al. | 607/5 |
| 5,334,221 | 8/1994 | Bardy | 607/14 |
| 5,350,401 | 9/1994 | Levine | 607/14 |
| 5,425,748 | 6/1995 | Pless | 607/5 |
| 5,425,749 | 6/1995 | Adams | 607/5 |
| 5,464,429 | 11/1995 | Hedberg et al. | 607/4 |

FOREIGN PATENT DOCUMENTS 0272021  7/1964  Australia .................................. 607/5

Primary Examiner—William E. Kamm
Assistant Examiner—Carl H. Layno
Attorney, Agent, or Firm—Brad D. Pedersen

[57] ABSTRACT

A method and apparatus for treating ventricular tachycardia arrhythmias using an ICD system delivers a series of stepped cardioversion pulses that include at least a first and second cardioversion countershock of low energy values that are less than about 5 joules. The energy values of each cardioversion countershocks increase in stepped progressions such that the low energy value of the first cardioversion countershock is less than the second and all subsequent cardioversion countershocks. The use of a series of stepped cardioversion pulses minimizes the possibility of "overstimulating" heart cells in any reentrant loop that are causing the ventricular tachycardia. As a result, the possibility of inducing fibrillation by the cardioversion therapy is significantly decreased. The leading edge of each of the series of stepped cardioversion pulses is sufficient to just stimulate any heart cells that are in phase 4, but is not strong enough to stimulate heart cells that are in phase 3. Thus, if a reentrant loop is within the reaches of the leading edge of a pulse, that reentrant loop is converted without the possibility of inducing fibrillation.

26 Claims, 6 Drawing Sheets

Fig. 1
Fig. 2
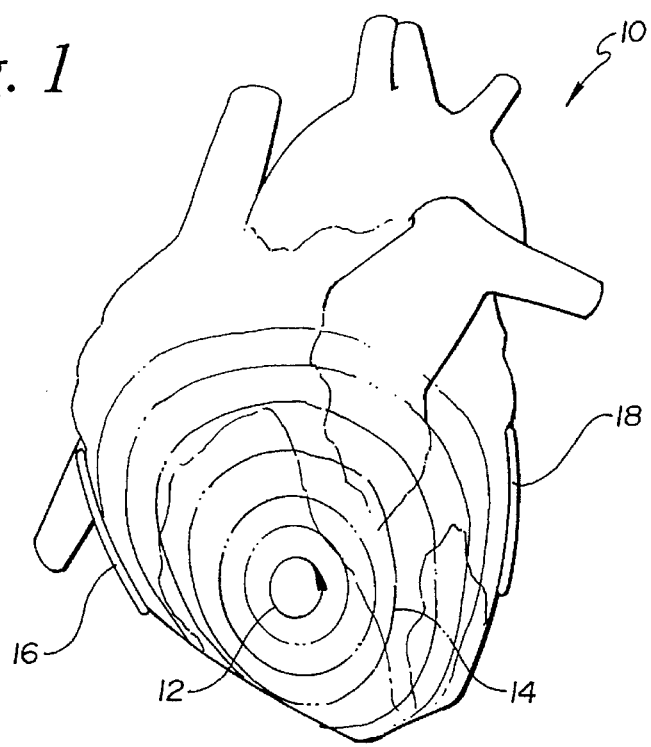
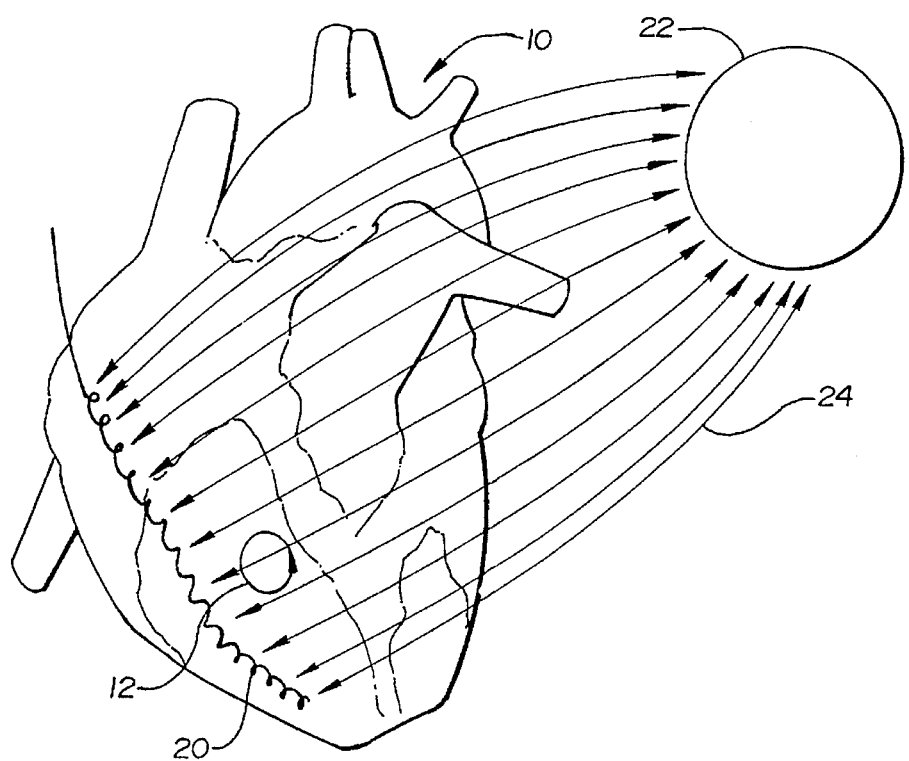

Fig. 5
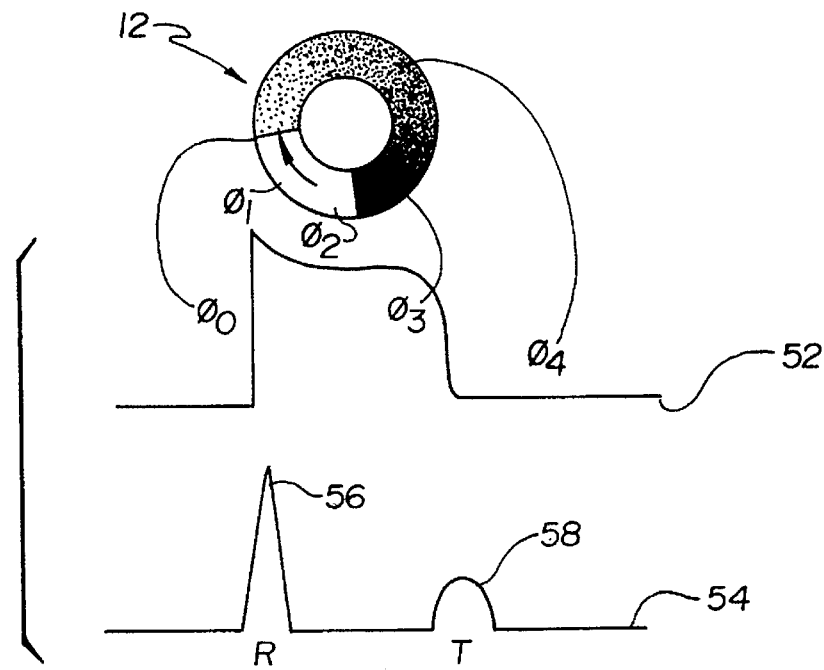
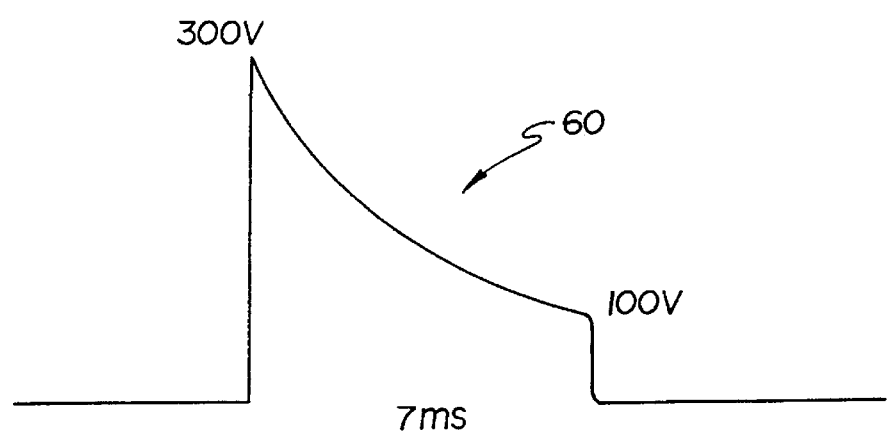
Fig. 6
PRIOR ART

STEPPED CARDIOVERSION SYSTEM FOR AN IMPLANTABLE CARDIOVERTER DEFIBRILLATOR

BACKGROUND

1. Field of the Invention

The present invention relates generally to cardioversion therapy as delivered by implantable cardioverter defibrillator (ICD) systems for treating ventricular tachycardias. More particularly, the present invention relates to a stepped cardioversion system that decreases the possibility of inducing fibrillation during delivery of cardioversion therapy by the ICD system.

2. Background of the Invention

The use of implantable cardioverter defibrillator (ICD) systems as a medical therapy for persons with abnormal heart conditions or arrhythmias is well known. Initially, ICD systems were used only to recessitate or defibrillate a heart which had stopped pumping because there was no organized heart beat. This type of arrhythmia, referred to as ventricular fibrillation (VF), is relatively simple to detect and is fatal if not corrected in a few minutes. The general approach in using an ICD systems to treat ventricular fibrillation is to deliver a relatively large electrical defibrillation countershock to electrodes implanted about the heart in an attempt to restart the electrical activity of the heart. In existing ICD systems, the defibrillation electrical countershocks are in the range of 25 to 40 joules, and are generated by high voltage capacitors within the ICD system that are charged to approximately 600 to 750 volts by an internal battery.

ICD systems are now being used to treat other types of abnormal heart conditions, such as the main pumping chambers of the heart beating too fast. This type of arrhythmia, referred to as ventricular tachycardia (VT) can be clinically divided into two subclasses. The first VT subclass is a low rate ventricular tachycardia where the heart is beating in the range of approximately 120 to about 180 beats per minute. While a low rate VT is not normal, the patient is not in immediate danger of dying because there is still a perfusing pulse that can pump blood to the body. The second VT subclass is a high rate ventricular tachycardia where the heart is beating in the range of approximately 180 to about 250 beat per minute. In contrast to low rate VT, a patient with a high rate VT is in imminent danger of death within the next several minutes due to a significantly diminished or absent perfusing pulse.

High rate VT, despite its severity and grim prognosis, is treated differently from ventricular fibrillation. This is because, unlike a VF arrhythmia where there is no organized electrical activity of the heart, a high rate VT arrhythmia still exhibits a fairly organized and synchronous electrical activity of the heart and often can be treated by delivering a synchronized "cardioversion" countershock of lower energy that is in the range of 1 to 5 joules. If this cardioversion countershock is unsuccessful, existing ICD systems immediately resort to the use of a defibrillation countershock due to the serious nature of the high rate VT arrhythmia.

Low rate VT is also characterized by a synchronized electrical activity of the heart, but a low rate VT is usually able to generate a perfusing pulse. As a result, it is important in treating a low rate VT to avoid subjecting the patient to an electrical cardioversion therapy that could convert the patient from an abnormal but life sustaining arrhythmia to an abnormal and terminal arrhythmia. Because a low rate VT can be inadvertently converted is not immediately life threatening, avoidance of shock pain is a major goal. Thus, the usual approach for low rate VT is to deliver bursts of overdrive pacing pulses that will pace the heart at a rate greater than the low rate tachycardia. This technique utilizes pacemaker level energies of approximately 10 to 50 microjoules per pulse for a burst duration of approximately 10 pulses per burst. If the first burst is unsuccessful and the patient remains in a low rate VT, subsequent bursts are reattempted. Unfortunately, even this "Anti-tachycardia" pacing can cause acceleration of the rhythm into a high rate tachycardia or even fibrillation.

In summary, while existing ICD systems have been used with some success to treat low rate and high rate ventricular tachycardias, there is a chance that the existing treatment therapies used by ICD systems for these types of arrhythmias can cause the arrhythmia to further deteriorate to a fatal ventricular fibrillation condition. Consequently, it would be desirable to provide a new treatment therapy for treating ventricular tachycardia arrhythmias using an ICD system that decreases the possibility of inducing fibrillation during delivery of the cardioversion therapy by the ICD system.

SUMMARY OF THE INVENTION

The present invention is a method and apparatus for treating ventricular tachycardia arrhythmias using an ICD system which delivers a series of stepped cardioversion pulses that include at least a first and second cardioversion countershock of low energy values that are less than about 5 joules. The energy values of each cardioversion countershocks increase in stepped progressions such that the low energy value of the first cardioversion countershock is less than the second and all subsequent cardioversion countershocks. The use of a series of stepped cardioversion pulses minimizes the possibility of "overstimulating" heart cells in any reentrant loop that are causing the ventricular tachycardia. As a result, the possibility of inducing fibrillation by the cardioversion therapy is significantly decreased. Like successive waves when a pebble is dropped in a pond, the leading edge of each of the series of stepped cardioversion pulses is sufficient to just stimulate any heart cells that are in phase 4, but is not strong enough to stimulate heart cells that are in phase 3. Thus, if a reentrant loop is within the reaches of the leading edge of a pulse, that reentrant loop is broken without the possibility of inducing fibrillation.

In accordance with a first aspect of the present invention, a method of operating an implantable cardioverter defibrillator system to treat ventricular tachycardias is provided. The implantable cardioverter defibrillator system is a self-contained human implantable device that includes a pulse-generating system for storing an electrical charge, an energy system for internally charging the pulse-generating system, a detection system for detecting a ventricular tachycardia in a human patient and a control system for selectively discharging the electrical charge as an electrical countershock to be delivered through two or more electrodes adapted for implantation in the human patient in response to the detection means. The method comprises the device-implemented step of: (a) delivering a first cardioversion countershock of a first low energy value of less than about 5 joules; and (b) delivering at least a second cardioversion countershock of a second low energy value of less than about 5 joules, the second low energy value being greater than the first low energy value.

In accordance with a second aspect of the present invention, an improved implantable cardioverter defibrillator system for treating ventricular tachycardias is provided. The implantable cardioverter defibrillator system is a self-contained human implantable device that includes a pulse-generating means for storing an electrical charge, an energy means for internally charging the pulse-generating system, means for detecting a ventricular tachycardia in a human patient and a control means for selectively discharging the electrical charge as an electrical countershock to be delivered through two or more electrodes adapted for implantation in the human patient in response to a means for detecting. The improvement to the implantable cardioverter defibrillator comprises the control means further including means for delivering a first cardioversion countershock of a first low energy value of less than about 5 joules; and means for delivering at least a second cardioversion countershock of a second low energy value of less than about 5 joules, the second low energy value being greater than the first low energy value.

DETAILED DESCRIPTION OF THE DRAWINGS

FIG. 1 is a schematic view of a human heart showing a reentrant loop of a ventricular tachycardia arrhythmia.

FIG. 2 is a schematic view of a human heart similar to FIG. 1, but showing an alternate electrode placement.

FIG. 5 is a graphic representation of the relationship between a reentrant loop, a single heart cell activation cycle, and a surface electrocardiogram (ECG) signal.

FIG. 6 is a graph showing a prior art cardioversion waveform.

DETAILED DESCRIPTION OF THE PREFERRED EMBODIMENT

Figure 3:
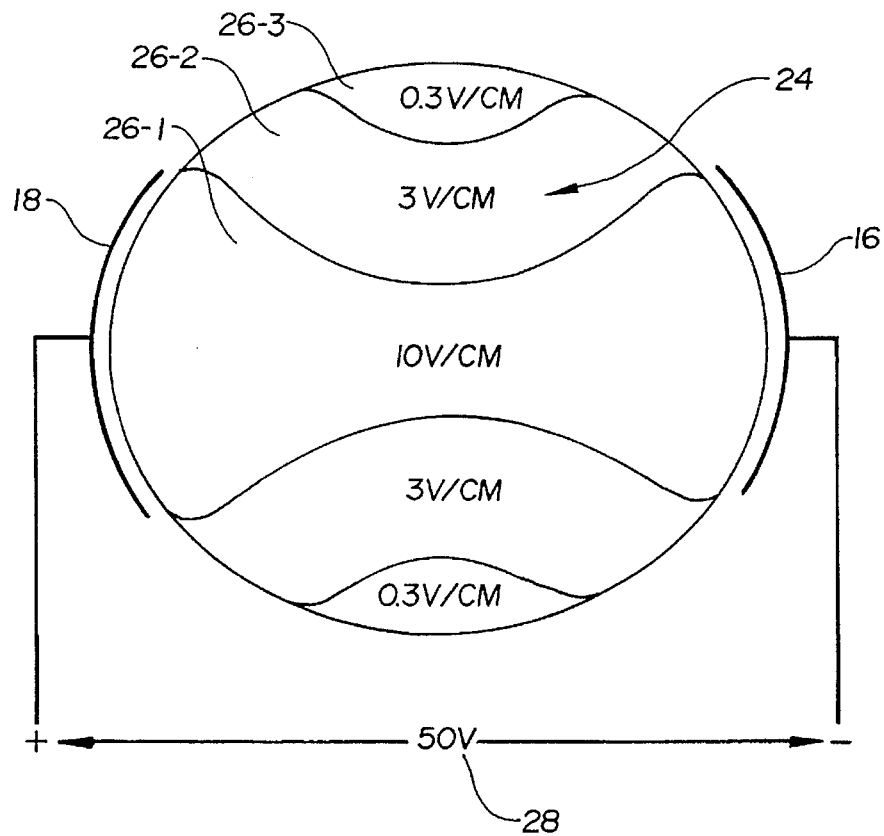
FIG. 3 is a schematic view of a human heart showing an electric field generated by a cardioversion countershock.

FIG. 1 shows a schematic view of a human heart 10. A ventricular tachycardia (VT) arrhythmia that is the focus of the present invention is typically caused by the electrical activity of a relatively small reentrant loop of heart cells 12. Reentrant loop 12 consists of a ring of heart cells having a diameter on the order of 1 cm which start activating each other in a sequence that is faster than the heart rate of the rest of heart 10. The electrical oscillation of reentrant loop 12 quickly spreads throughout the heart cells in the rest of heart 10, as shown for example at 14, thereby causing an excessive heart rate condition known as VT. In this case, only one reentrant loop 12 is shown, however, it is also possible to have a VT arrhythmia caused by multiple reentrant loops 12, a condition which is referred to as a polymorphR VT.

While the exact reasons why a reentrant loop 12 begins to oscillate or fire out of sequence are not known, it is known that in order to stop the VT arrhythmia any and all reentrant loops 12 in heart 10 must be extinguished. If a reentrant loop 12 is not extinguished, then the VT will most likely continue.

One way to extinguish reentrant loops 12 is to pass an electrical current through heart 10 in the form of a cardioversion countershock of between about 100–300 V. The goal of the cardioversion countershock is to stimulate enough heart cells in reentrant loop 12 so as to stop the electrical oscillation and return those heart cells to a normal heart rate. In FIG. 1, a cardioversion countershock is delivered across heart 10 by discharging a predetermined voltage between a pair of electrodes, such as epicardial patch electrodes 16 and 18, for a relatively short period of time. In FIG. 2, a cardioversion countershock is delivered across heart 10 by discharging a predetermined voltage between a right ventricular coil electrode 20 and a subpectoral patch or device housing electrode 22. In either case, the discharge of the voltage across the electrodes generates an electrical field across heart 10.

As shown in FIG. 3, the field 24 produced by a cardioversion countershock will vary as shown by field zones shown as 26-1 to 26-3 that extend between electrodes 16 and 18, for example. The exact values of the fields will depend primarily upon the value of the discharge voltage, as shown at 28, and the electrode placement of the heart 10. Generally, electrical field 24 is strongest closest to electrodes 16 and 18 and will be weaker further away from the electrodes.

Figure 4:
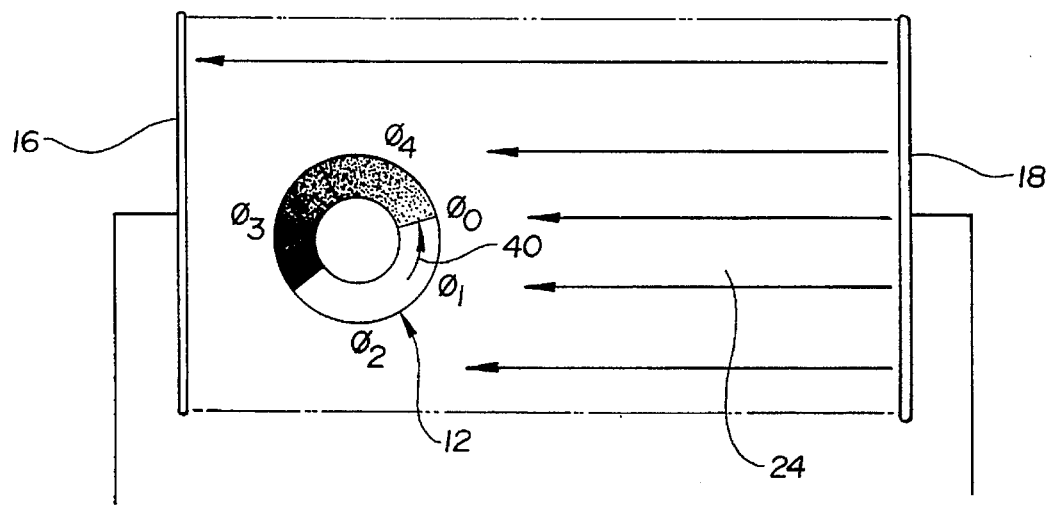
FIG. 4 is a more detailed schematic view of a heart including a reentrant loop showing the various phases of electrical cellular activity.

The mechanism by which the electrical field produced by a cardioversion countershock can override the electrical activity of heart cells in a reentrant loop can be understood by reference to FIG. 4. FIG. 4 shows a more detailed schematic view of a reentrant loop 12. A reentrant wave of electrical activity, represented by arrow 40, shows the oscillating electrical activity of heart cells in reentrant loop 12. All of the cells in reentrant loop 12 go through different phases as reentrant wave 40 cycles around loop 12.

At the head of wave 40, the heart cells are in the process of being electrically activated. Cells in this area of loop 12 are said to be in phase 0. Next are heart cells which have just been activated (phase 1) and heart cells which are in a stable activated state (phase 2). When heart cells are in any of these three phases (phase 0, 1 or 2), it is extremely difficult to stimulate the heart cells via an external electrical field because these cell have just been or are being stimulated. These phases are often referred to as the "absolute refractory period" because cells in these phases are not amenable to stimulation by anything other than a very strong external electrical fields of the magnitude typically reserved for delivering defibrillation countershocks. Further back in wave 40, there is a group of heart cells (phase 3) that are beginning to recover from the stimulation at phase 0 and are said to be in a "relative refractory period". Finally, at the end of wave 40 are heart cells (phase 4) which have fully recovered from the stimulation at phase 0 and are said to be at a "resting potential" or in a "electrical diastole period". Heart cells in phase 4 are very amenable to stimulation from external electrical fields that are of relatively low gradients (less than 1 V/cm), compared to the relatively high gradients of the electrical fields required for defibrillation (greater than 10 V/cm).

The idea behind a cardioversion countershock is to stimulate or "catch" the heart cells in reentrant loop 12 when they are in phase 4 by using a low gradient electrical field developed between electrodes 16 and 18. The stimulation of the heart cells of reentrant loop 12 during phase 4 prevents the progression of reentrant wave 40 and will usually abolish the VT arrhythmia. When the head of reentrant wave 40 encounters heart cells which were in phase 4, but which have now been stimulated by the low gradient electrical field, these cells can no longer continue the cyclic activity of reentrant wave 40, and the reentrant loop is abolished. By analogy, the low gradient electrical field acts as the lighting of a small back fire which stops the advance of a larger fire by burning all of the fuel ahead of the larger fire.

FIG. 5 shows a graphic representation of the relationship between a reentrant loop 12, a single heart cell activation cycle 52, and a surface electrocardiogram (ECG) signal 54. Note that reentrant loop 12 is shown proceeding in a clockwise manner in this FIG. so as to correspond with the convention for portraying cell activation cycles and ECG signals. The collective activation of heart cell in phase 0 results in the spiked ECG component known as the R-wave or QRS complex, as shown at 56. The more gradual recover of the heart cells in phase 3 results in the rounded ECG component known as the T-wave, as shown at 58.

It is known that electrical countershocks of moderate strength delivered during the T-wave can sometimes cause fibrillation. This is due to the fact that during the T-wave the heart cells are generally in a relative refractory period where some of the cells are recovered and are very amenable to activation by an external electrical field and some of the cells are not recovered. As a result, activation waves generated by an external electrical field can proceed through the heart in unpredictable directions and along complex paths, as opposed to cleanly progressing throughout the heart muscle in accordance with the path of a normal heart beat. These unpredictable activation waves can sometimes induce a fibrillation of the heart muscle. It is for this reason that the prior art cardioversion techniques have attempted to synchronize the delivery of a cardioversion countershock to a sensing of the R-wave.

FIG. 6 shows a typical prior art cardioversion waveform 60 which would be delivered by an implantable cardioverter defibrillator (ICD) to treat a VT. Waveform 60 has an initial voltage of 300 V, a trailing voltage of about 100 V and a pulse width of about 7 ms. Waveform 60 is delivered by the ICD as a truncated-capacitive discharge from a capacitor system that is internally charged by a battery within the ICD. A description of a prior art cardioversion waveform 60 delivered synchronously with an R-wave can be found in U.S. Pat. No. 4,384,585. Examples of existing ICD systems that have been approved by the Federal Drug Administration to deliver a cardioversion waveform 60 are the Medtronic PCD®, the Cardiac Pacemaker Ventak®, and the Ventritex Cadence®.

The problem with the prior art cardioversion waveform 60 is that, even if waveform 60 is delivered synchronously with a sensed R-wave such that most of the heart cells are at the start of the absolute refractory period (phase 0), there will be some heart cells in the reentrant loop which are in the dangerous relative refractory period (phase 3) because the electrical activation of reentrant loop 12 will not be synchronized with the general ECG signal of the heart. In other words, even though the cardioversion countershock is properly timed for all but a few of the heart cells, namely those cells in reentrant loop 12 that are in phase 3, if those few heart cells are stimulated in an unpredictable manner, they can possibly initiate a domino effect that would cause a fibrillation of the entire heart.

Because of this risk of inducing fibrillation, the currently accepted practice for delivering a cardioversion countershock is to deliver a single cardioversion waveform 60, wait for a few seconds for the heart to recover and then sense to determine if the VT arrhythmia was abolished. If the VT was not abolished, a higher energy countershock is delivered.

Figure 7:
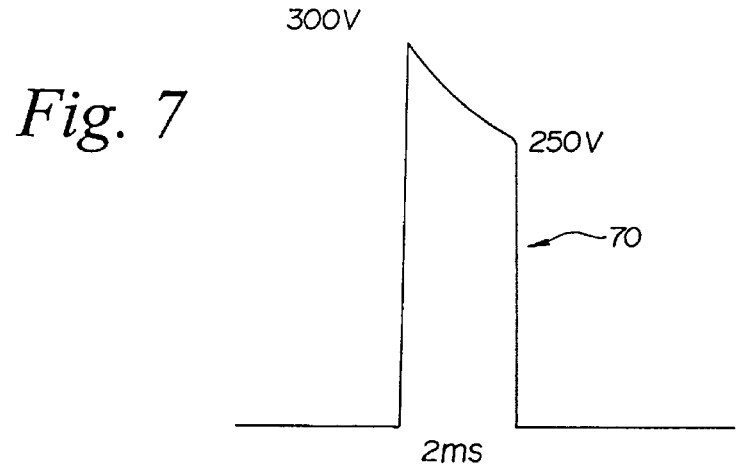
FIG. 7 is a graphic representation of a narrow cardioversion waveform.

FIG. 7 shows a narrow cardioversion waveform 70 which results in improved performance over the prior art cardioversion waveform 60. Narrowing the pulse width of cardioversion waveform 70 to about 2 ms more closely matches the duration of cardioversion waveform 70 to the cardioversion chronaxie time period of a human heart. This shorter time period results in a more efficient pacing of the heart cells in phase 4 and a less efficient stimulation of any heart cells that are in the vulnerable phase 3. For a more detailed description of the operation of the narrow cardioversion waveform, reference is made to a co-pending application filed in the United States Patent and Trademark Office on Apr. 9, 1992, Ser. No. 07/866,460, now issued as U.S. Pat. No. 5,334,219 entitled "SHORT PULSE CARDIOVERSION SYSTEM FOR AN IMPLANTABLE CARDIOVERTER DEFIBRILLATOR", and assigned to the same assignee as the present invention, the disclosure of which is hereby incorporated by reference.

Figure 8:
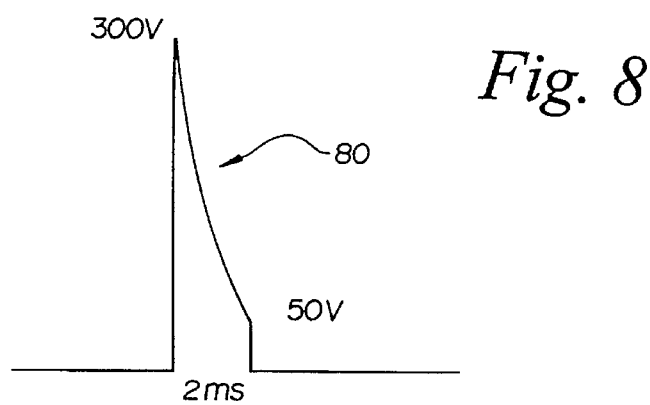
FIG. 8 is a graphic representation of an alternate embodiment of a narrow cardioversion waveform.

FIG. 8 shows an alternate embodiment of a narrow cardioversion waveform 80. Cardioversion waveform 80 differs from cardioversion waveform 70 in that it is delivered from a capacitor system that is separate from the capacitor system in an ICD that is used to deliver defibrillation countershocks. As a result, cardioversion waveform 80 is a more efficient waveform that achieves the goals of matching the cardioversion chronaxie in the same way as cardioversion waveform 70, but without wasting the energy remaining at the end of the countershock. For a more detailed description of the operation of the separate capacitor narrow cardioversion waveform, reference is made to a co-pending application filed in the United States Patent and Trademark Office on Apr. 9, 1992, Ser. No. 07/866,368, now issued as U.S. Pat. No. 5,334,219 entitled "IMPROVED METHOD AND APPARATUS FOR SEPARATE-CAPACITOR CARDIOVERSION", the disclosure of which is hereby incorporated by reference in the present application.

Even though cardioversion waveforms 70 and 80 decrease the risk of inducing fibrillation by delivery of a cardioversion countershock, these waveforms do not directly address the fundamental timing problem inherent in delivery of a cardioversion countershock. Returning to FIG. 3, it can be seen that there is a wide range of field gradients 26 generated for any given discharge voltage 28. Typically, electrical field 24 is strongest closest to electrodes 16 and 18, as shown, for example, in zone 26-1 which represents a 10 V/cm electric field for a discharge voltage of 50 V. At the edges of heart 10, electric field 24 is much weaker, as shown in zone 26-3 represents a 0.3 V/cm electric field for a discharge voltage of 50 V. Thus, the actual value of electric field 24 which is used to stimulate a reentrant loop 12 will vary greatly for an identical discharge voltage 28 depending upon where that reentrant loop 12 is located relative to electrodes 16 and 18. If a reentrant loop 12 occurs at a location near the apex of heart 10 and away from electrodes 16 and 18, the electric field in zone 26-3 at only 0.3 V/cm is simply too small to stimulate any of the heart cells in phase 4. As a result, the cardioversion countershock would fail to convert the VT arrhythmia and standard procedure would dictate the use of a defibrillation countershock to treat the VT arrhythmia. Conversely, if a reentrant loop 12 occurs at a location very near electrodes 16 and 18, then the electric field in zone 26-1 at nearly 10 V/cm is high enough to not only stimulate cells in phase 4 and phase 3, but would even stimulate cells in the absolute refractory period as this level of electric field is high enough to be used as a defibrillation countershock. In this case, the VT arrhythmia caused by reentrant loop 12 would be converted, but more energy than was necessary would have been expended from the ICD system and the cardioversion countershock would have been more powerful, and potentially more painful, than might otherwise be necessary.

The most dangerous condition for a cardioversion countershock therapy, however, is when a reentrant loop 12 occurs at a location near the middle of heart 10. In this situation, the electric field in zone 26-2 at 3 V/cm is not enough to stimulate and synchronize heart cells in all of the phases, including the absolute refractory period, but is enough to stimulate heart cells in reentrant loop 12 that are in the vulnerable phase 3 condition. Consequently, there is a possibility that a conventional cardioversion countershock used to treat a reentrant loop 12 at this location would actually cause a lethal VF arrhythmia.

The susceptibility of heart cells in the various phases to different levels of average electric fields is summarized in Table I. The average electric fields represented in Table I would be measured over 1 cc of heart cells at any location in the heart that is not directly adjacent (i.e., more than 1 mm away from) electrodes 16 or 18. Heart cells located directly adjacent the implanted electrodes of an ICD system typically experience electrical fields that are very non-linear with respect to the actual discharge voltage applied to the electrodes, therefore an analysis of average electrical fields in the regions is not very meaningful. Beyond the region directly adjacent the implanted electrodes, however, the concept of an average electrical field at a given location within the heart does have meaning, particularly when taken in the context of the theory set forth by the present invention. For relatively low electric fields between about 0.5 V/cm and 2.0 V/cm, only heart cells in phase 4 are stimulated. For more moderate electric fields between about 2.5 V/cm and 10 V/cm, heart cells in phase 3 may also be stimulated in addition to the heart cells in phase 4. For relatively high electric fields that are greater than about 10 V/cm, most of the heart cells will be stimulated, including those in the absolute refractory period. Finally, for very high electric fields that are greater than about 20 V/cm, all of the heart cells would be stimulated, regardless of phase.

TABLE I

| Average Electric Field | Heart Cell Phase | | |
| --- | --- | --- | --- |
| | Phase 1/2 | Phase 3 | Phase 4 |
| 0.5–2.0 V/cm | nothing | nothing | stimulate |
| 2.5–10.0 V/cm | nothing | fibrillate? | stimulate |
| 10.0–20.0 V/cm | stimulate? | stimulate | stimulate |
| 20.0 + V/cm | stimulate | stimulate | stimulate |

It will be understood that the term stimulate as applied to heart cells which are already in the activation phases (phases 1 or 2) should be construed to mean a broad-sense stimulation or a prolongation of the activation potential. It should also be emphasized that the exact values of electric fields required to stimulate heart cells in each phase will vary significantly, depending upon the type of heart, the individual, the pulse width of the electrical countershock, and whether any drugs have been previously used in an attempt to treat the VT. For a more detailed discussion of the problems of applying moderate electrical fields to the heart which may stimulate heart cells that are in vulnerability, reference is made to Chen, P. et al., "Comparison of the defibrillation threshold and the upper limit of ventricular vulnerability", *Circulation* 73, No. 5, 1022–1028, 1986.

Figure 9:
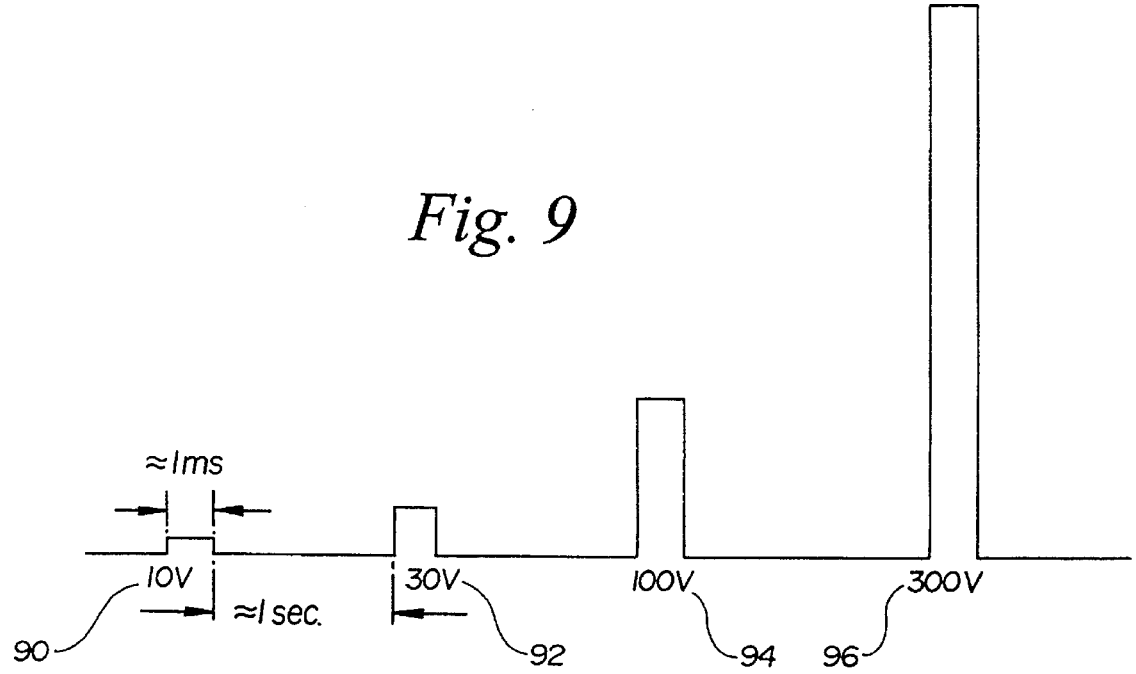
FIG. 9 is a graphic representation of a preferred embodiment of a series of stepped cardioversion pulses for a cardioversion waveform in accordance with the present invention.

Referring now to FIG. 9, the cardioversion therapy of the present invention will be described. In contrast to the existing techniques for cardioversion therapy which deliver a single cardioversion countershock followed by a defibrillation countershock if the cardioversion countershock is unsuccessful, the present invention delivers a series of stepped cardioversion pulses. The present invention uses a series of stepped cardioversion pulses in an effort to eliminate the possibility of "overstimulating" a reentrant loop 12, thereby inducing the possibility of fibrillation. For loops closest to the electrodes, the first pulse of the series of stepped cardioversion pulses is sufficient to just stimulate any heart cells that are in phase 4, but is not strong enough to stimulate heart cells that are in phase 3. Thus, if a reentrant loop 12 is within the reaches of the leading edge of a pulse, that reentrant loop 12 would be converted without the possibility of inducing fibrillation.

As shown in FIG. 9, the stepped cardioversion pulses 90, 92, 94 and 96 start at very low voltages and each succeeding pulse increases in amplitude over the preceding pulse. Unlike conventional cardioversion pulses which have discharge voltages ranging from 50 to 300 V, the initial cardioversion pulse 90 has a discharge voltage that is greater than 5 V but less than 20 V, and preferably about 10 V. This low initial discharge voltage is chosen such that any electric field gradients immediately adjacent the electrodes will be greater than 0.5 V/cm and less than about 2.0 V/cm so as to only stimulate heart cells which are in a phase 4 condition. Thus, even in the worst case situation where a reentrant loop 12 were located proximate the electrodes (i.e., greater than 1 mm away from but not more than 1 cm away from the electrodes), the electric field gradient on the first stepped pulse 90 is not high enough to stimulate heart cells in a phase 3 condition. As a result, the risk of inducing fibrillation by delivery of the first stepped pulse 90 is significantly decreased, if not altogether eliminated.

As can also been seen from FIG. 9, each subsequent pulse 92, 94 and 96 after the first stepped pulse 90 increases in a stepwise manner the discharge voltage of the cardioversion countershock. As will be shown, the effect of each subsequent pulse 92, 94 and 96 is to extend the outermost voltage gradient of the cardioversion countershock that will stimulate heart cells in a phase 4 condition from a boundary just beyond the region in the heart where the previous countershock ended stimulating heart cells in a phase 4 condition.

Figure 10:
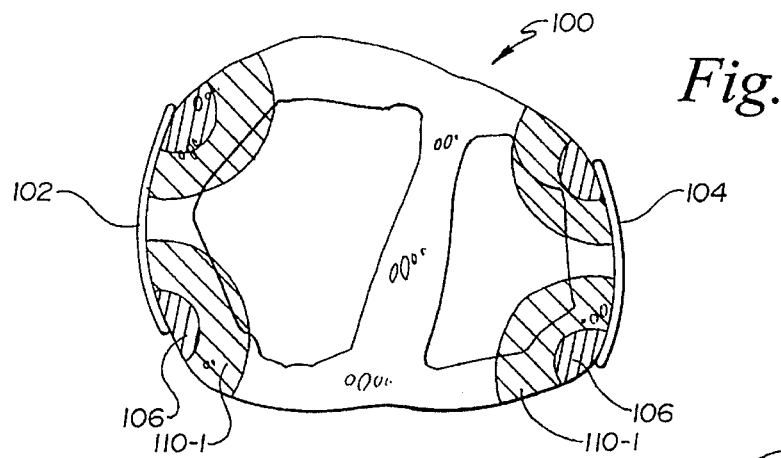
FIGS. 10, 11, 12 and 13 are a series a simplified schematic diagrams of a cross section of a heart showing the contiguous electrical gradients of a series of cardioversion pulses delivered in accordance with FIG. 9.
Figure 11:
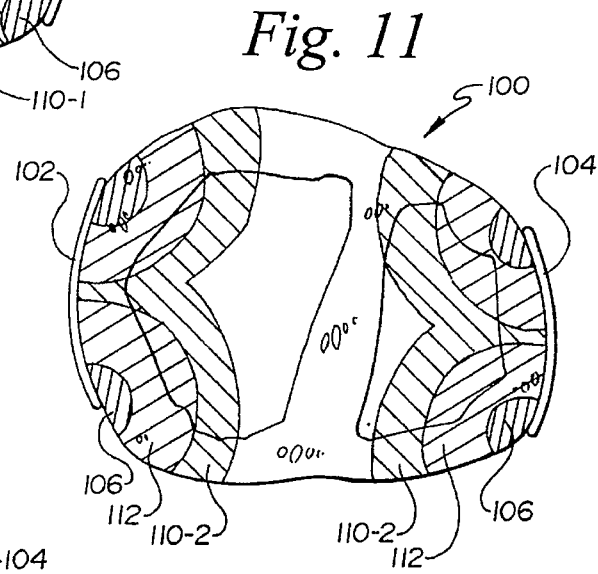
Figure 12:
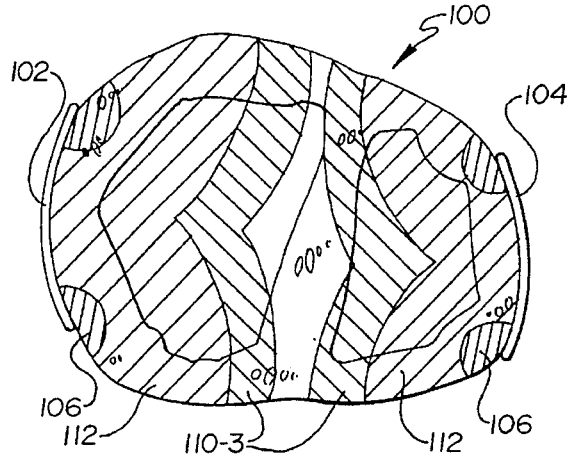
Figure 13:
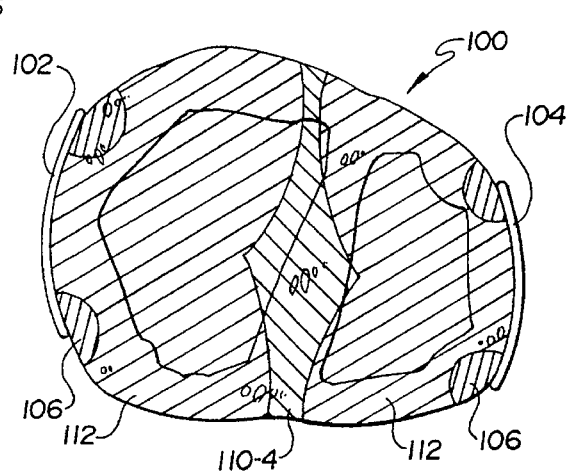

Referring now to FIGS. 10, 11, 12 and 13, a comparison of the voltage gradients across a section of a heart 100 is presented for the series of stepped pulses 90, 92, 94 and 96 as shown in FIG. 9. In FIGS. 10, 11, 12 and 13, a simplified top view cross section of a heart 100 is shown between a pair of epicardial patch electrodes 102 and 104. In FIG. 10, the first of the series of stepped pulses 90 is applied to electrodes 102 and 104. At electrode regions 106 which are directly adjacent electrodes 102 and 104, and, in this case, particularly the end or edge portions of electrodes 102 and 104 experience a high electric field which is essentially linear to that of the applied voltage across electrodes 102 and 104. In leading edge regions 110-1, however, the relatively low applied voltage of stepped pulse 90 creates an electrical field across these areas of the heart where only heart cells which are in phase 4 are stimulated. It can be seen from FIG. 10 that no other regions of heart 100 are stimulated. In FIG. 11, the second of the series of stepped pulses 92 is applied to electrodes 102 and 104. Again, electrode regions 106 are present at the edges of electrodes 102 and 104 and, leading edge regions 110-2 are present along the leading edge of where an electrical field of stimulating level is applied across heart 100. In contrast to FIG. 10, however, a second region 112 is also present between electrode regions 106 and leading edge regions 110. In these second regions 112, the gradient of the electrical field is sufficient to stimulate and, hence, capture heart cells which are in phases other than phase 4. A similar situation is shown in both FIGS. 12 and 13 corresponding to the delivery of stepped pulses 94 and 96 which creates leading edge regions 110-3 and 110-4, respectively.

The staggering of the stepped pulses in accordance with the present invention results in leading edge regions 110-1, 110-2, 110-3 and 110-4 that provide "phase 4 voltage gradients" for each subsequent pulses 90, 92, 94 and 96. Each phase 4 voltage gradient, in the form of leading edge regions 110, represents that portion of the cardioversion countershock where the voltage gradients are sufficient to stimulate heart cells in a phase 4 condition but are not sufficient to stimulate heart cells in a phase 3 condition. Ideally each subsequent phase 4 voltage gradients 110 will just overlap each the previous phase 4 voltage gradient, although in practice there may be varying degrees of overlap due to variation in the electrical fields which develop in each individual heart in response to a discharge voltage of a given level.

In the embodiment shown in FIGS. 9–13, the discharge voltages for pulses 90, 92, 94 and 96 are chosen at 10 V, 30 V, 100 V and 300 V, respectively. In a preferred embodiment, the voltage increase between successive pulses 90, 92, 94 and 96 is set between a range of at least about two times the voltage of the previous pulse to no more than five time the voltage of the previous pulse. The maximum value for this range of increase ratios is established based on the difference in the range of electrical fields required for phase 3 stimulation (i.e., 0.5–2.0 V/cm) as compared to the range of electrical fields required for phase 3 fibrillation (2.5–10 V/cm). Optimally, the voltage increase between successive pulses 90, 92, 94 and 96 is about three times the voltage of the preceeding pulse.

It will be recognized that the number of pulses and the values for each discharge voltage can be varied in numerous ways and still achieve the objective of the present invention. For example, depending upon the particular electrode configuration, a cardioversion countershock may be more or less efficient at delivering the electrical energy to the heart. In addition, the size and shape of each of the regions 106, 110 and 112 may vary significantly between patients and with varying electrode configurations. For example, the size and shape of regions 106 will generally be a function of the particular shape and configuration of electrodes 102 and 104. Consequently, a series of stepped pulses for a cardioversion countershock delivered by two spaced apart electrodes on an RV catheter might need an entirely different set of stepped pulses than a series of stepped pulses delivered between a pair of epicardial patch electrodes. In addition, it is understood that while at least two electrodes 102 and 104 are required to deliver the cardioversion countershock, these electrodes may be any known combination of electrodes and may also include more than two electrodes, as well as steering of the cardioversion countershock among the electrodes during a countershock or between successive cardioversion countershocks.

Ideally, at the time that an ICD system is implanted, the attending physician will determine an optimum number of stepped pulses and optimum discharge voltage values for each pulse that are within the ranges given by the present invention, but that also are based on the individual parameters of the particular patient. For a more detailed discussion of the implication of electrode configuration and placement on the generation of electrical fields across the heart, reference is made to Ideker et al., "Current Concepts for Selecting Location, Size and Shape of Defibrillation Electrodes", *PACE*, Vol. 14, Feb. 1991, Part I, pp. 227–240, and Tang et al., "Three-dimensional Potential Gradient Fields Generated by Intracardiac Catheter and Cutaneous Patch Electrodes", *Circulation*, Vol. 85, No. 5, May 1992, pp. 1857–1864.

In a preferred embodiment, each subsequent pulse 92, 94 and 96 is delivered within greater than about 0.25 seconds and less than about 1 second from the previous pulse. Ideally, each pulse 90, 92, 94 and 96 is delivered on the R-wave of a series of subsequent heart beats as sensed through an ECG signal. Unlike prior art ICD systems, the present invention is able to deliver pulses 90, 92, 94 and 96 with these relatively short time intervals between pulses. In the preferred embodiment, each pulse 90, 92, 94 and 96 is a short cardioversion pulse 70 or 80, as previously described in connection with FIGS. 7 and 8. Because the capacitor system used to deliver cardioversion pulse 80, for example, is more efficient, less energy, and hence less time, is required to charge the capacitor system. Thus, recharging can occur within the relatively short time interval between pulses. In addition, the recharge time for pulses 90, 92, and 94 is shorter because the discharge voltage values are generally smaller than the discharge voltage values typically used for cardioversion countershocks.

Figure 14:
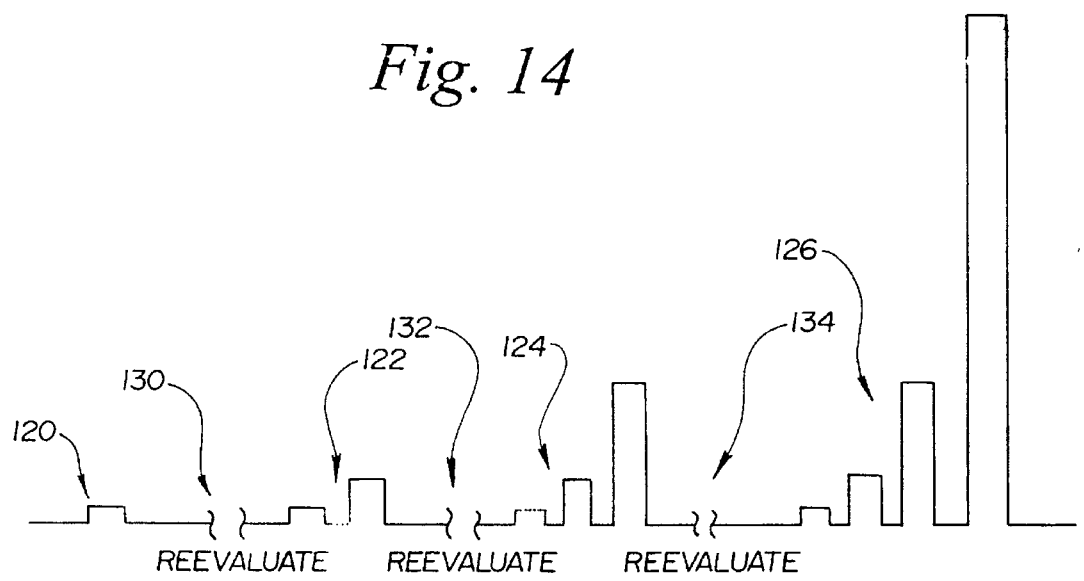
FIG. 14 is a graphic representation of an alternate embodiment of a series of stepped cardioversion pulses that for a cardioversion waveform in which provide for a confirmation of continuing ventricular tachycardia during delivery of the series of stepped cardioversion pulses.

It will be understood that the delivery of pulses 90, 92, 94 and 96 in this manner would effectively preclude any inter-countershock sensing to determine whether the VT arrhythmia had been converted. This is because the normal time period required for effective sensing after delivering of an electrical countershock requires a few seconds for the heart and sensing electrodes to recover and be able to provide an ECG signal which could be effectively used to determine whether the VT had been converted. In an alternate embodiment as shown in FIG. 14, intershock confirmation is provided during delivery of a series of stepped cardioversion pulses. In this embodiment, a determination is made as to whether the stepped cardioversion therapy in the form of one or more stepped cardioversion pulses was successful in extinguishing a detected VT. If the stepped cardioversion therapy was successful, then the therapy is terminated. If the stepped cardioversion therapy was not successful, additional sequences of stepped cardioversion therapy are attempted that included the previously delivered stepped cardioversion pulse plus an additional stepped cardioversion pulse delivered at a higher voltage.

As shown in FIG. 14, a first set of stepped cardioversion pulses 120 consisting of a single relatively low voltage is applied, producing a resultant electrical field similar to that shown in FIG. 10. After waiting for the heart and sensing electrodes to recover, a detection 130 is made to determine whether the therapy was successful in terminating the VT arrhythmia. If first stepped cardioversion pulse 120 is not successful, a second set of stepped cardioversion pulses 122 consisting of a first relatively low voltage followed by a second somewhat higher voltage, the second pulse being delivered within about 1 second from the first pulse. This second set of stepped cardioversion pulses 122 produces sequential resultant electrical fields similar to those shown in FIG. 10 and then FIG. 11. Again, a detection 132 is made to confirm whether the therapy was successful. If not successful, a third set of stepped cardioversion pulses 124 consisting of three separate stepped pulses is delivered and, if that set is not successful as determined by detection 134, a fourth set of stepped cardioversion pulses 126 consisting of four separate stepped pulses may be delivered.

By arranging the delivery of sets of stepped pulses 120, 122, 124 and 126 combined with detections 130, 132 and 134 in this manner, the alternate embodiment allows for therapy to be stopped if the VT arrhythmia is converted prior to delivery of any of the sets of stepped pulses. As a result, any combination of monomorphR VT or polymorphR VT which would totally reside within one of the leading edge regions 110 will be converted, as well as any combination of monomorphR VT or polymorphR VT which resides partially between two successive leading edge regions will also be converted.

In the first example of a monomorphR VT reentrant loop 12 residing totally within a single leading edge region 110, the stepped pulse 120, 122, 124 or 126 that is associated with the leading edge region in which the mononode VT reentrant loop 12 resides will convert the VT arrhythmia. Before the mononode VT reentrant loop 12 is converted, each detection period 130, 132 or 134 would continue to detect the presence of a VT arrhythmia and the therapy would be continued. In this case, it would not be medically necessary to repeat the earlier lower voltage stepped cardioversion pulses as the leading edge regions 110 associated with those pulses did not contain the reentrant loop 12. The case of a polymorphR VT in which each of a multiple number of reentrant loops was completely within a leading edge region would also not necessarily require a repetition of earlier delivered stepped pulses 90, 92 or 94 upon detection of a continued VT.

Because the exact number and locations of reentrant loops 12 causing a VT are not diagnosable by current detection techniques, it is not possible to separate either the first or second condition in which the reentrant loop is totally within a leading edge region from a partial overlap condition where a reentrant loop 12 crossed the boundary of two adjacent leading edge regions 110. Such a partial overlap condition requires repetition of the earlier lower voltage stepped pulses as part of the next set of stepped pulses 122, 124 or 126 in order to avoid causing that portion of the partial overlap in the first leading edge region 110 to fibrillate during a subsequent delivery of a higher voltage stepped pulses in an attempt to capture the portion of the reentrant loop in the second leading edge region 110. It will be apparent that the partial overlap condition can apply to either a monomorphR VT or polymorphR VT which partially overlaps adjacent leading edge regions 110.

To cover all three possibilities, the alternate embodiment simply repeats the earlier delivered stepped pulses after redetection of a VT arrhythmia as part of a subsequent set of stepped cardioversion pulses 122, 124 or 126. In this way, the patient is spared the unnecessary use of higher voltage stepped cardioversion pulses in the event that a lower voltage stepped cardioversion pulse converted the VT. The ICD system also conserves valuable stored energy by not delivering unneeded therapy. Most importantly, however, the delivery of the therapy is accomplished in a manner which minimizes the possibility of advancing a VT into any type of life threatening VF. As a result, the present invention makes it possible to treat low rate VT by using cardioversion level therapy, instead of overdrive pacing, without incurring the risk of creating a potential VF.

Figure 15:
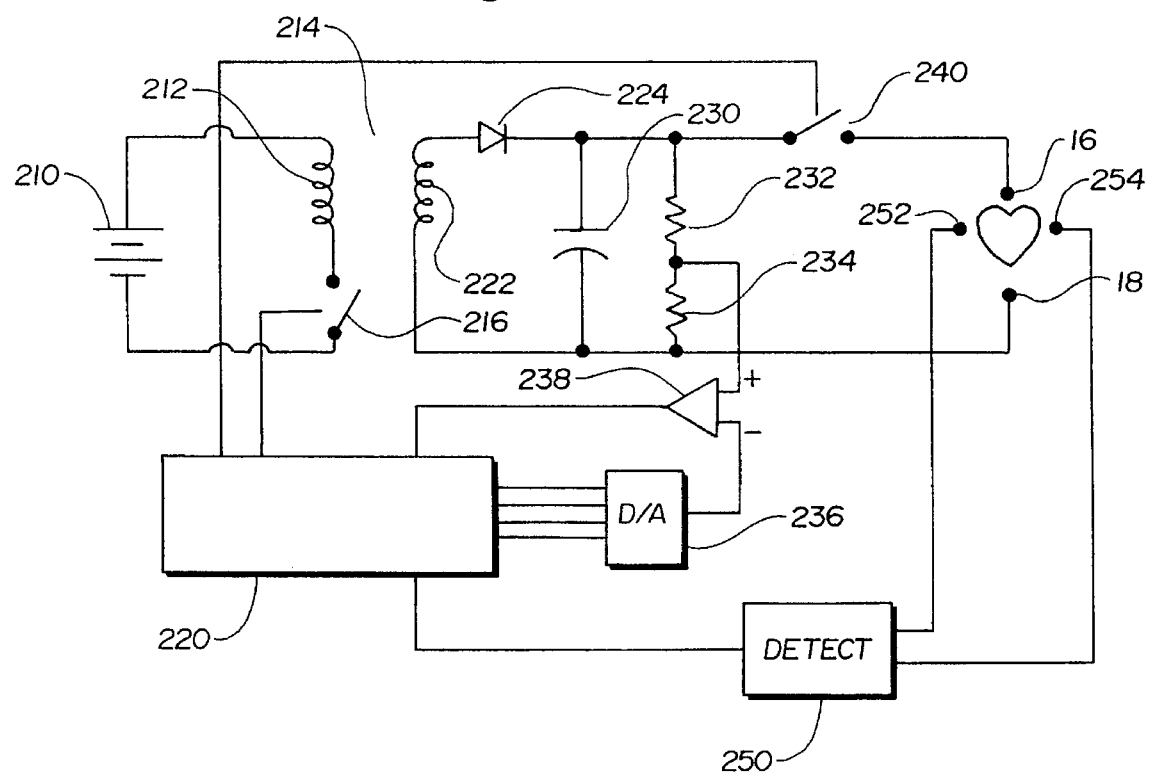
FIG. 15 is a schematic diagram of an electrical circuit for generating a series of cardioversion pulses in accordance with a preferred embodiment of the present invention.

Referring now to FIG. 15, a schematic diagram of a preferred embodiment for circuitry to implement the present invention within an ICD system will be described. In FIG. 15, a battery system 210 supplies a current to a primary winding 212 of transformer 214 which is interrupted at a high frequency through switch 216 that is controlled by microcontroller 220. A high voltage is generated on a secondary winding 222 of transformer 214 which is rectified by diode 224 and stored in energy storage capacitor system 230. The output voltage on capacitor system 230 is reduced from up to a very high voltage in the hundreds of volts to a measuring level of a few volts by a resistor divider network comprised of resistors 232 and 234. The output of the resistor divider network is supplied to a comparator 238, the input of which is connected to a digital-to-analog (D/A) converter 236 which is in turn connected to microcontroller 220 such that microcontroller 220 can instantaneously monitor the charging voltage seen on capacitor system 230. Once a desired charging voltage for the particular cardioversion countershock pulse has been achieved, the charging action of transformer 214 is ceased and the ICD system is ready to deliver the cardioversion pulse by having microcontroller 220 activate switch 240 in response to detection circuitry 250 that is shown connected to sensing electrodes 252, 254. Switch 240 connects the output of capacitor system 230 with electrodes 16 and 18. Alternatively, switch 240 could be replaced by a conventional H-bridge circuit controlled by microcontroller 220 so as to deliver a biphasic waveform for each cardioversion pulse 90, 92, 94 and 96. It will be recognized that many types of known detection circuitry 250 can be employed with the present invention. In the event that a defibrillation countershock is indicated after attempts at cardioversion have failed, it will be recognized that capacitor system 230 may be charged to deliver such a defibrillation countershock (in which case switch 256, for example, may be used to disable the voltage divider network 232, 234). Alternatively, a separate capacitor system 260 may be charged (in which case switches 262 and 264, for example, may be used to disable capacitor system 230 and voltage divider network 232, 234).

I claim:

1. A method of operating an implantable cardioverter defibrillator system to treat ventricular tachycardias, the implantable cardioverter defibrillator system being a self-contained human implantable device that includes a high voltage pulse-generating capacitor system for storing an electrical charge, an energy system for internally charging the pulse-generating capacitor system, a detection system for detecting a ventricular tachycardia in a human patient and a control system for selectively discharging the electrical charge as an electrical countershock to be delivered through at least two electrodes adapted for implantation in the human patient in response to the detection means, the method comprising the device-implemented step of:

(a) delivering a first cardioversion countershock of a first low energy value of less than about 4.99 joules from the pulse-generating capacitor system; and (b) delivering at least a second cardioversion countershock of a second low energy value of less than about 4.99 joules from the pulse-generating capacitor system, the second low energy value being greater than the first low energy value.

2. The method of claim 1 wherein the second cardioversion countershock is delivered within less than one second from the first cardioversion countershock.

3. The method of claim 1 wherein the first cardioversion countershock produces an electrical field adjacent the electrodes through which the countershock is delivered that is less than about 2.5 V/cm.

4. The method of claim 1 wherein the first low energy value is less than about 2 joules.

5. The method of claim 1 wherein the first low energy value has an initial voltage value of less than about 20 V.

6. The method of claim 5 wherein the first low energy value has an initial voltage value of less than about 10 V.

7. The method of claim 1 wherein at least three cardioversion countershocks are delivered in step (b) each having a low energy value that is larger than the low energy value of the preceding cardioversion countershock.

8. The method of claim 1 wherein the second cardioversion countershock is spaced apart from the first cardioversion countershock by at least 0.25 seconds.

9. The method of claim 1 wherein the second cardioversion countershock has a voltage value that is between two times to five times greater than a voltage value of the first cardioversion countershock.

10. The method of claim 9 wherein the second cardioversion countershock has a voltage value that is about three times greater than a voltage value of the first cardioversion countershock.

11. The method of claim 1 further comprising the step of:

(c) confirming detection of a continued ventricular tachycardia prior to delivery of the second cardioversion countershock in step (b).

12. The method of claim 10 further comprising the step of:

(d) upon detection of the continued ventricular tachycardia in step (c), repeating step (a) within 1 second prior to performing step (b).

13. An improved implantable cardioverter defibrillator system for treating ventricular tachycardias, the implantable cardioverter defibrillator system being a self-contained human implantable device that includes a high voltage pulse-generating capacitor means for storing an electrical charge, an energy means for internally charging the pulse-generating capacitor means, means for detecting a ventricular tachycardia in a human patient and a control means for selectively discharging the electrical charge as an electrical countershock to be delivered through at least two electrodes adapted for implantation in the human patient in response to a means for detecting, the improvement comprising:

the control means further including:

means for delivering a first cardioversion countershock of a first low energy value of less than about 4.99 joules from the pulse-generating capacitor means; and means for delivering at least a second cardioversion countershock of a second low energy value of less than about 4.99 joules from the pulse-generating capacitor means, the second low energy value being greater than the first low energy value.

14. The system of claim 13 wherein control means delivers the second cardioversion countershock within less than one second from the first cardioversion countershock.

15. The system of claim 13 wherein the control means limits the first low energy value is less than about 2 joules.

16. The system of claim 13 wherein the control means limits the first low energy value to an initial voltage value of less than about 20 V.

17. The system of claim 16 wherein the control means limits the first low energy value to an initial voltage value of less than about 10 V.

18. The system of claim 13 wherein the control means delivers the first cardioversion countershock at a voltage such that the first cardioversion countershock produces an electrical field adjacent the electrodes through which the countershock is delivered that is less than about 2.5 V/cm.

19. The system of claim 13 wherein the means for delivering at least the second cardioversion countershock delivers at least three cardioversion countershocks, each having a low energy value that is larger than the low energy value of the preceding cardioversion countershock.

20. The system of claim 13 wherein control means delivers the second cardioversion countershock such that the second cardioversion countershock is spaced apart from the first cardioversion countershock by at least 0.25 seconds.

21. The system of claim 13 wherein the control means delivers the second cardioversion countershock at a voltage value that is between two times to five times greater than a voltage value of the first cardioversion countershock.

22. The system of claim 21 wherein the control means delivers second cardioversion countershock at a voltage value that is about three times greater than a voltage value of the first cardioversion countershock.

23. The system of claim 13 wherein the control means further comprises:

means for confirming detection of a continued ventricular tachycardia prior to delivery of the second cardioversion countershock.

24. The system of claim 23 wherein the control means comprises:

means for redelivering the first cardioversion countershock within 1 second prior to delivering the second cardioversion countershock upon detection of the continued ventricular tachycardia.

25. The system of claim 21 wherein the pulse-generating capacitor means comprises:

a first capacitor means for delivering the first and second cardioversion countershocks; and a second capacitor means for delivering a defibrillation countershock.

26. The system of claim 25 wherein the first capacitor means has an effective capacitance that is smaller than an effective capacitance of the second capacitor means.

* * * * *